(12) United States Patent
Yamashita et al.

(10) Patent No.: US 9,400,247 B2
(45) Date of Patent: Jul. 26, 2016

(54) AUTOMATIC ANALYZER

(71) Applicant: HITACHI HIGH-TECHNOLOGIES CORPORATION, Tokyo (JP)

(72) Inventors: Kotaro Yamashita, Tokyo (JP); Masahiko Iijima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 169 days.

(21) Appl. No.: 14/379,356

(22) PCT Filed: Feb. 12, 2013

(86) PCT No.: PCT/JP2013/053203
§ 371 (c)(1),
(2) Date: Aug. 18, 2014

(87) PCT Pub. No.: WO2013/125386
PCT Pub. Date: Aug. 29, 2013

(65) Prior Publication Data
US 2015/0033831 A1 Feb. 5, 2015

(30) Foreign Application Priority Data

Feb. 24, 2012 (JP) .................................. 2012-039158

(51) Int. Cl.
*G01N 21/03* (2006.01)
*G01N 21/11* (2006.01)
(Continued)

(52) U.S. Cl.
CPC .............. *G01N 21/55* (2013.01); *G01N 21/253* (2013.01); *G01N 21/274* (2013.01); *G01N 21/51* (2013.01);
(Continued)

(58) Field of Classification Search
CPC .............. G01N 2021/0325; G01N 2021/0389; G01N 2021/115; G01N 2021/155; G01N 2021/157; G01N 2021/1736; G01N 2021/3129; G01N 2021/513; G01N 2021/825; G01N 2035/009; G01N 21/15; G01N 21/51; G01N 21/55; G01N 21/253; G01N 21/274; G01N 21/78; G01N 21/82; G01N 35/00; G01N 35/00623; G01N 2201/0415; G01N 33/48; G01N 33/49; G01N 33/493
See application file for complete search history.

(56) References Cited

U.S. PATENT DOCUMENTS 4,227,886 A 10/1980 Bullock et al.
6,791,676 B1 9/2004 Meller
(Continued)

FOREIGN PATENT DOCUMENTS

EP 2023147 A2 2/2009
EP 2541233 A1 1/2013
(Continued)

OTHER PUBLICATIONS

Extended European Search Report received in corresponding European Application No. 13751468.3 dated Sep. 15, 2015.
(Continued)

*Primary Examiner* — Joseph S Wong
(74) *Attorney, Agent, or Firm* — Mattingly & Malur, PC

(57) ABSTRACT

An automatic analyzer has a multi-wavelength light source that irradiates a reaction cuvette containing a liquid mixture of a sample to be analyzed and a reagent. A transmitted-light quantity detector detects the amount of light transmitted through the reaction cuvette and internal contents of the reaction cuvette. A single-wavelength light source irradiates the reaction cuvette with single-wavelength light; and a transmitted-light quantity detector detects the amount of single-wavelength light scattered from the reaction cuvette. A memory stores the results of the transmitted-light quantity detection and the scattered-light quantity detection; and the deterioration states of the single-wavelength light source, multi-wavelength light source, and reaction cuvette are determined in accordance with measurement results of cell blank measurements conducted on the reaction cuvette where a predetermined reference solution is stored to detect the amount of light transmitted through and the amount of light scattered from.

5 Claims, 6 Drawing Sheets

| SCATTERED LIGHT \ TRANSMITTED LIGHT | CBa0-CBa1>THca | CBa0-CBa1≦THca |
|---|---|---|
| CBs0-CBs1>THcs | CELL CHECK ALARM<br>1. DIRTY IRRADIATION WINDOWS AND SENSOR WINDOWS OF SCATTERED-LIGHT QUANTITY MEASURING UNIT AND TRANSMITTED-LIGHT QUANTITY MEASURING UNIT<br>2. DIRTY INCUBATOR BATH<br>3. DIRTY REACTION CUVETTE<br>4. MALFUNCTIONING SINGLE-WAVELENGTH LIGHT SOURCE AND MULTI-WAVELENGTH LIGHT SOURCE | LED CHECK ALARM<br>1. DIRTY IRRADIATION WINDOW AND SENSOR WINDOW OF SCATTERED-LIGHT QUANTITY MEASURING UNIT<br>2. MALFUNCTIONING SINGLE-WAVELENGTH LIGHT SOURCE |
| CBs0-CBs1≦THcs | LAMP CHECK ALARM<br>1. DIRTY IRRADIATION WINDOW AND SENSOR WINDOW OF TRANSMITTED-LIGHT QUANTITY MEASURING UNIT<br>2. MALFUNCTIONING MULTI-WAVELENGTH LIGHT SOURCE | NO ALARM |

(51) Int. Cl.
*G01N 21/15* (2006.01)
*G01N 21/17* (2006.01)
*G01N 21/31* (2006.01)
*G01N 21/51* (2006.01)
*G01N 21/82* (2006.01)
*G01N 35/00* (2006.01)
*G01N 21/55* (2014.01)
*G01N 21/25* (2006.01)
*G01N 21/27* (2006.01)
*G01N 21/78* (2006.01)
*G01N 33/48* (2006.01)
*G01N 33/49* (2006.01)
*G01N 33/493* (2006.01)

(52) U.S. Cl.
CPC ............... *G01N 21/78* (2013.01); *G01N 21/82* (2013.01); *G01N 33/48* (2013.01); *G01N 33/49* (2013.01); *G01N 33/493* (2013.01); *G01N 35/00* (2013.01); *G01N 35/00623* (2013.01); *G01N 2021/0325* (2013.01); *G01N 2021/0389* (2013.01); *G01N 2021/3129* (2013.01); *G01N 2021/513* (2013.01); *G01N 2021/825* (2013.01); *G01N 2035/009* (2013.01); *G01N 2201/0415* (2013.01)

(56) References Cited

U.S. PATENT DOCUMENTS

| | | | |
|---|---|---|---|
| 2009/0017544 | A1 | 1/2009 | Iguchi et al. |
| 2010/0277727 | A1* | 11/2010 | Schlaminger .......... G01N 21/15 356/326 |
| 2013/0302212 | A1* | 11/2013 | Wakui .................... G01N 21/51 422/82.05 |

FOREIGN PATENT DOCUMENTS

| | | |
|---|---|---|
| JP | 2001-091518 A | 4/2001 |
| JP | 2001-141654 A | 5/2001 |
| JP | 2002-296284 A | 10/2002 |
| JP | 2004-251802 A | 9/2004 |
| JP | 2009-20059 A | 1/2009 |
| JP | 2011-174842 A | 9/2011 |

OTHER PUBLICATIONS

International Preliminary Report on Patentability received in International Application No. PCT/JP2013/053203 dated Sep. 4, 2014.

* cited by examiner

FIG. 6

| SCATTERED LIGHT \ TRANSMITTED LIGHT | CBa0−CBa1>THca | CBa0−CBa1≦THca |
|---|---|---|
| CBs0−CBs1>THcs | CELL CHECK ALARM<br><br>1. DIRTY IRRADIATION WINDOWS AND SENSOR WINDOWS OF SCATTERED-LIGHT QUANTITY MEASURING UNIT AND TRANSMITTED-LIGHT QUANTITY MEASURING UNIT<br><br>2. DIRTY INCUBATOR BATH<br><br>3. DIRTY REACTION CUVETTE<br><br>4. MALFUNCTIONING SINGLE-WAVELENGTH LIGHT SOURCE AND MULTI-WAVELENGTH LIGHT SOURCE | LED CHECK ALARM<br><br>1. DIRTY IRRADIATION WINDOW AND SENSOR WINDOW OF SCATTERED-LIGHT QUANTITY MEASURING UNIT<br><br>2. MALFUNCTIONING SINGLE-WAVELENGTH LIGHT SOURCE |
| CBs0−CBs1≦THcs | LAMP CHECK ALARM<br><br>1. DIRTY IRRADIATION WINDOW AND SENSOR WINDOW OF TRANSMITTED-LIGHT QUANTITY MEASURING UNIT<br><br>2. MALFUNCTIONING MULTI-WAVELENGTH LIGHT SOURCE | NO ALARM |

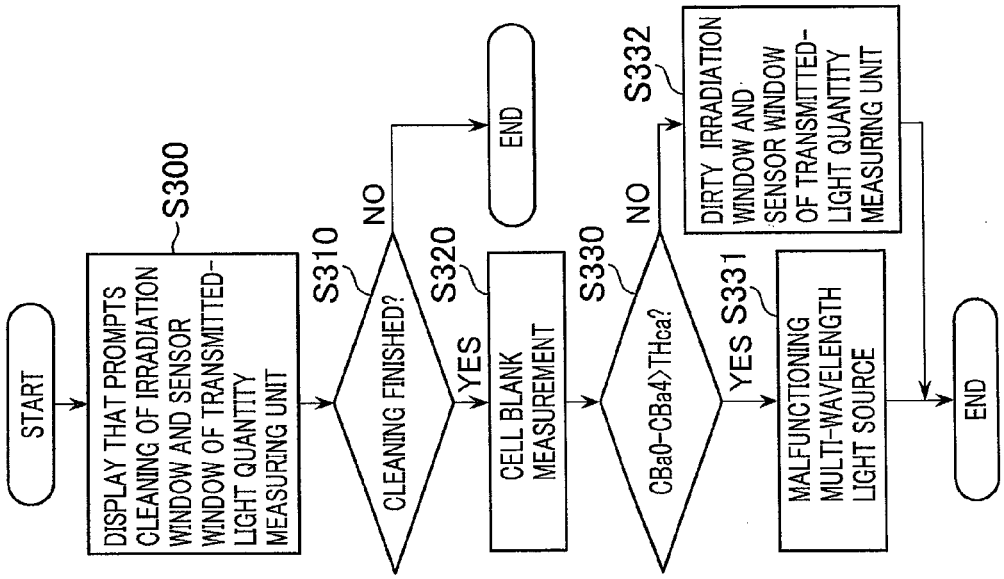

FIG. 11

| ALARM | LIGHT SOURCE | CBa0-CBa4>THca | CBa0-CBa4≤THca |
|---|---|---|---|
| LAMP CHECK ALARM | TRANSMITTED LIGHT | MALFUNCTIONING MULTI-WAVELENGTH LIGHT SOURCE | DIRTY IRRADIATION WINDOW AND SENSOR WINDOW OF TRANSMITTED-LIGHT QUANTITY MEASURING UNIT |

FIG. 12

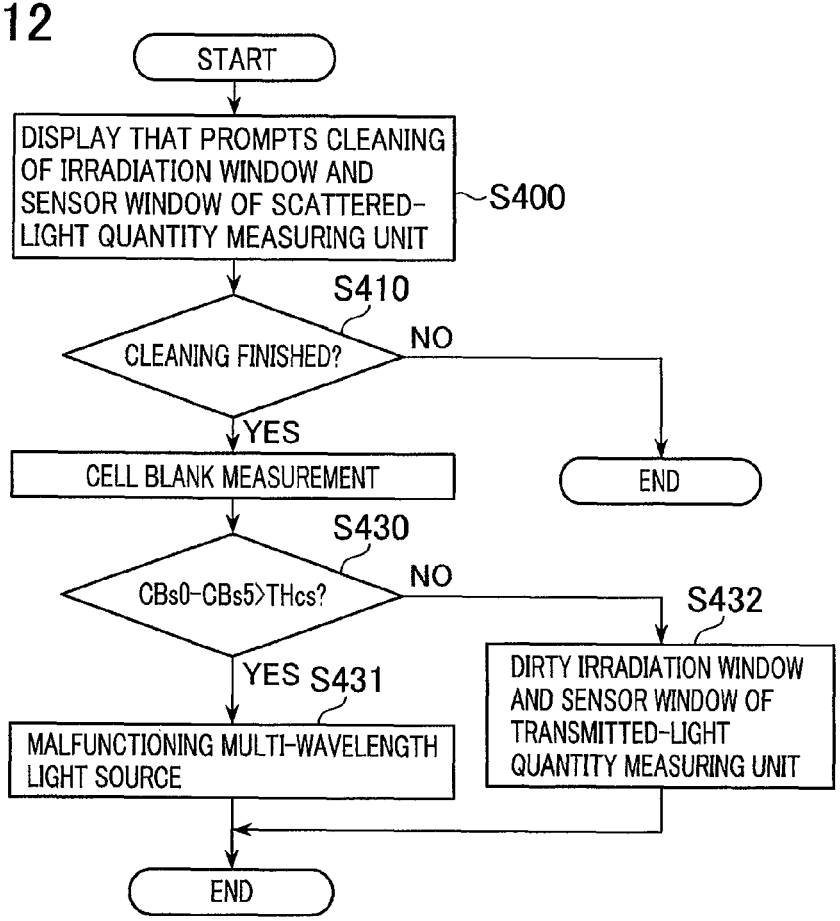

FIG. 13

| ALARM | LIGHT SOURCE | CBs0-CBs5>THcs | CBs0-CBs4≤THcs |
|---|---|---|---|
| LED CHECK ALARM | SCATTERED LIGHT | MALFUNCTIONING MULTI-WAVELENGTH LIGHT SOURCE | DIRTY IRRADIATION WINDOW AND SENSOR WINDOW OF SCATTERED-LIGHT QUANTITY MEASURING UNIT |

AUTOMATIC ANALYZER

TECHNICAL FIELD

The present invention relates to an automatic analyzer that conducts qualitative/quantitative analyses upon blood, urine, and other biological samples.

BACKGROUND ART

Automatic analyzers have a qualitative/quantitative analysis on blood, urine, and other biological samples in various ways. An example of its method is known to conduct the qualitative/quantitative analysis of samples by measuring the amount of light transmitted through a mixed reaction solution of the sample and a reagent, or by measuring the amount of light scattered by the reaction solution.

For example, Patent Document 1 (JP-2009-20059-A) discloses such an automatic analyzer, which employs a technique designed to determine whether a reaction cuvette for causing a reaction between a sample and a reagent and analyzing the sample can be actually used for measurement. Prior to the determination in this conventional technique, a reaction cuvette blank value that accretes with increasing changes in absorbance of a light beam transmitted through the reaction cuvette is compared with a plurality of determination criteria in which a different blank reference value is defined for each of analytical items. That is to say, the determination of the reaction cuvette for usability in the measurement is based primarily upon comparison results obtained from those comparisons.

RELATED TECHNICAL LITERATURE

Patent Document

Patent Document 1: JP-2009-20059-A

SUMMARY OF THE INVENTION

Problem to be Solved by the Invention

However, in addition to the reaction cuvette itself, a variety of other factors are involved with analytical accuracy of the automatic analyzer used for the qualitative/quantitative analysis of the sample. Thus it had been difficult to maintain high analytical accuracy by merely determining the reaction cuvette for usability, as in the above prior art.

The present invention has been made in the light of the above, and an object of the invention is to provide an automatic analyzer adapted to suppress a decrease in analytical accuracy.

Means for Solving the Problem

In order to attain the above object, an aspect of the present invention includes: a multi-wavelength light source that irradiates with multi-wavelength light a reaction cuvette containing a liquid mixture of a sample to be analyzed and a reagent; means that detects the amount of light transmitted through the reaction cuvette and internal contents of the reaction cuvette; a single-wavelength light source that irradiates the reaction cuvette with single-wavelength light; means that detects the amount of single-wavelength light scattered from the reaction cuvette and the internal contents of the reaction cuvette; a storage unit for storing a result of the transmitted-light quantity detection with the transmitted-light quantity detection means and a result of the scattered-light quantity detection with the scattered-light quantity detection means; and a determining unit that performs a deterioration determining process to determine deterioration states of the single-wavelength light source, multi-wavelength light source, and reaction cuvette in accordance with measurement results of cell blank measurements conducted on the reaction cuvette where a predetermined reference solution is stored to detect the amount of light transmitted through, and the amount of light scattered from.

Advantages

In the present invention, the decrease in analytical accuracy can be suppressed.

BRIEF DESCRIPTION OF THE DRAWINGS

FIG. 6 is a diagram showing an example of determination results on deterioration.

FIG. 8 is a diagram showing another example of determination results on deterioration.

FIG. 9 is a diagram showing yet another example of determination results on deterioration.

FIG. 10 is a flowchart of a maintenance support process relating to a lamp check alarm.

FIG. 11 is a diagram showing a further example of determination results on deterioration.

FIG. 12 is a flowchart of a maintenance support process relating to an LED check alarm.

FIG. 13 is a diagram showing a further example of determination results on deterioration.

MODE FOR CARRYING OUT THE INVENTION

An embodiment of the present invention will be described below with reference to the accompanying drawings.

Figure 1:
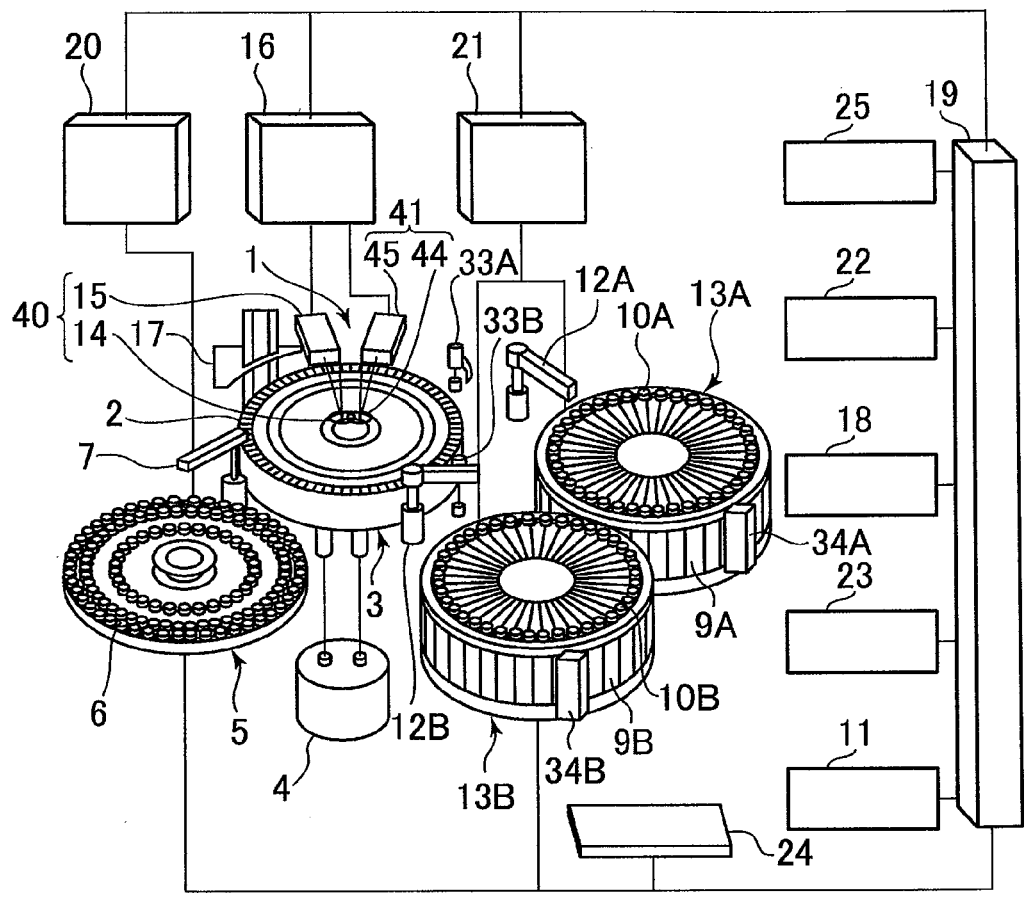
FIG. 1 is a diagram showing schematically an overall configuration of an automatic analyzer according to an embodiment of the present invention.
Figure 2:
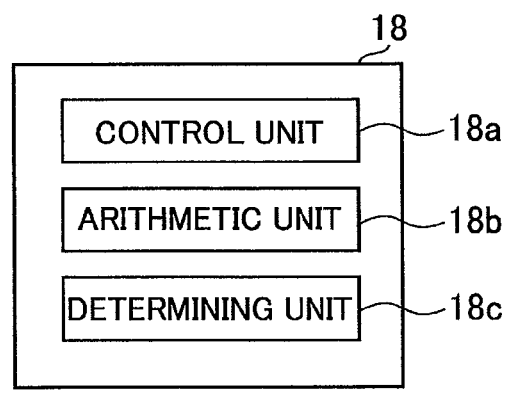
FIG. 2 is a functional block diagram showing a detailed functional configuration of a computer.
Figure 3:
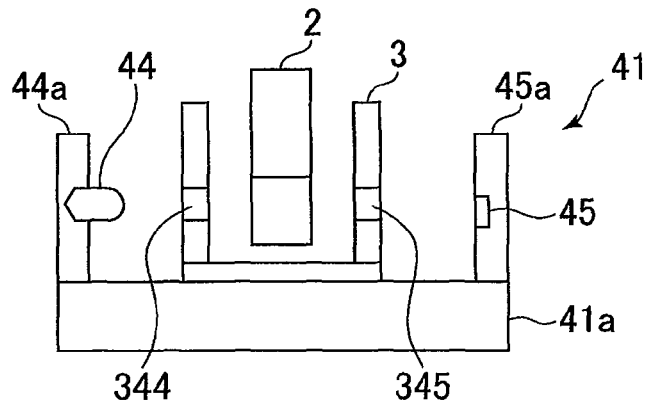
FIG. 3 is an enlarged view showing a transmitted-light quantity measuring unit.
Figure 4:
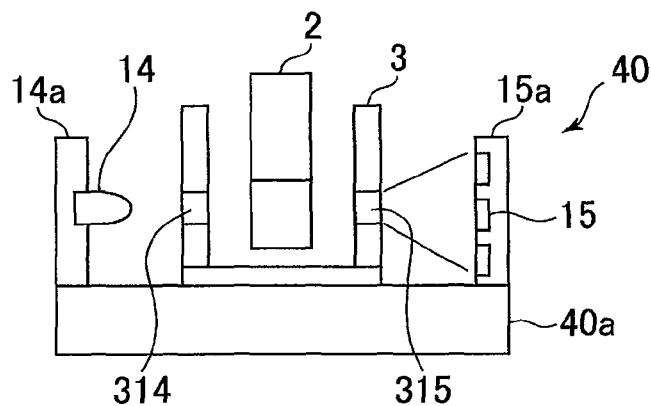
FIG. 4 is an enlarged view showing a scattered-light quantity measuring unit.

FIG. 1 is a diagram showing schematically an overall configuration of an automatic analyzer according to the present embodiment, and FIG. 2 is a functional block diagram showing a detailed functional configuration of a computer. In addition, FIGS. 3 and 4 are enlarged views showing a transmitted-light quantity measuring unit and a scattered-light quantity measuring unit, respectively.

Referring to FIG. 1, the automatic analyzer includes a samples disk 5, a first reagent disk 13A, a second reagent disk 13B, a reaction disk 1, a sampling mechanism 7, reagent dispensing mechanisms 12A, 12B, and other functional sections including a computer 18.

A plurality of sample containers 6, each containing blood, urine, or any other sample to be analyzed, are arranged side by side in a circumferential direction on the samples disk 5. The samples disk 5 is driven by a rotational driving mechanism (not shown) to rotate in the circumferential direction of the samples disk 5, thereby moving the sample containers 6 to a predetermined position.

The first and second reagent disks 13A, 13B include a reagent disk 9A or 9B, respectively. On each of the reagent disks 13A, 13B, a plurality of reagent bottles 10A, 10B, each containing a reagent to be used for the automatic analyzer to assess various analytical items, are arranged side by side in a circumferential direction of the reagent disk. The first and second reagent disks 13A, 13B are each driven by a rotational driving mechanism (not shown) to rotate in the circumferential direction of the reagent disk, thereby moving each of the reagent bottles 10A, 10B to a predetermined position. A reader 34A, 34B that reads reagent identification information provided on each reagent bottle 10A, 10B is further disposed on the first and second reagent disks 13A, 13B. After the reagent identification information has been read, this information is sent, along with information indicating a position of the reagent bottle on the first or second reagent disk 13A, 13B, to the computer 18 via an interface 19, and then stored in association with a date/time of the measurement and other information into a memory 11. For example, the reagent identification information is expressed in a form of a bar code and the readers 34A, 34B are bar code readers.

The reaction disk 1 includes a incubator bath (reaction vessel) 3 controlled to have a predetermined temperature by a constant-temperature keeping unit 4. On the reaction disk 1, a plurality of reaction cuvettes (reaction cells) 2, each for storing a mixed reaction solution formed by stirring and mixing the sample and the reagent, are arranged side by side in a circumferential direction of the reaction disk. The reaction disk 1 is driven by a rotational driving mechanism (not shown) to rotate in the circumferential direction of the reaction disk, thereby moving the reaction cuvettes 2 to a predetermined position.

The sampling mechanism 7 dispenses the sample, stored in each sample container 6, into the reaction cuvettes 2. And the reagent dispensing mechanisms 12A, 12B each dispense the reagent stored in each reagent bottle 10A, 10B, into the reaction cuvettes 2. The sample and reagent that have thus been dispensed into the reaction cuvettes 2 are next stirred and mixed by stirring mechanisms 33A and 33B disposed at respective dispensing positions close to the reagent dispensing mechanisms 12A, 12B.

Operations of the samples disk 1 and sampling mechanism 7 are controlled by a sampling control unit 20. Operation of the first and second reagent disks 13A, 13B, reagent dispensing mechanisms 12A, 12B, and stirring mechanisms 33A, 33B, are controlled by a reagent dispensing control unit 21. The sampling control unit 20 and the reagent dispensing control unit 21 are controlled by the computer 18 connected via the interface 19.

The transmitted-light quantity measuring unit 41 that performs a transmitted-light quantity detection process upon the sample and reagent stored as a mixed reaction solution in each reaction cuvette 1, and the scattered-light quantity measuring unit 40 that performs a scattered-light quantity detection process upon the mixed reaction solution are provided at the reaction disk 1. The transmitted-light quantity measuring unit 41 and the scattered-light quantity measuring unit 40 are described in further detail below.

As shown in FIG. 3, the transmitted-light quantity measuring unit 41 includes a multi-wavelength light source 44, for example a halogen light source, that irradiates with multi-wavelength light the reaction cuvette 2 containing the mixed reaction solution of the sample to be analyzed and the reagent. The transmitted-light quantity measuring unit 41 also includes transmitted-light quantity detectors 45 that each detect the amount of light transmitted through the reaction cuvette 2 and the mixed reaction solution stored therein. The transmitted-light quantity measuring unit 41 further has a base member 41a, a light source base 44a fixed to the base member 41a and serving as a base for disposing the multi-wavelength light source 44, and a detector base 45a fixed to the base member 41a and serving as a base for disposing the transmitted-light quantity detectors 45.

In the transmitted-light quantity measuring unit 41, the incubator bath 3 is disposed between the multi-wavelength light source 44 and the transmitted-light quantity detectors 45 so as to extend in the circumferential direction of the reaction disk 1. An irradiation window 344 and a sensor window 345 are positioned on a line connecting the multi-wavelength light source 44 and the transmitted-light quantity detectors 45 inside the incubator bath 3. The irradiation window 344 transmits the multi-wavelength light emitted from the multi-wavelength light source 44 toward the reaction cuvette 2. The sensor window 345 allows the light to further pass through the reaction cuvette 2 and reach the transmitted-light quantity detectors 45. The amount of transmitted light is detected whenever the reaction cuvette 2 driven in the circumferential direction of the reaction disk 1 inside the incubator bath 3 passes between the multi-wavelength light source 44 and each transmitted-light quantity detector 45. The amount of transmitted light that the transmitted-light quantity detector 45 has thus detected, that is, a detection result, is converted into a digital form by an A/D converter 16 and then sent to the computer 18 via the interface 19.

As shown in FIG. 4, the scattered-light quantity measuring unit 40 includes a single-wavelength light source 14, for example a light-emitting diode (LED) light source, that irradiates with single-wavelength light the reaction cuvette 2 containing the mixed reaction solution of the sample to be analyzed and the reagent. The scattered-light quantity measuring unit 40 also includes scattered-light quantity detectors 15 that each detect the amount of scattered light generated from the reaction cuvette 2 and the mixed reaction solution stored therein, the single-wavelength light being generated due to the irradiation of the single-wavelength light. The scattered-light quantity measuring unit 40 further has a base member 40a, a light source base 14a fixed to the base member 40a and serving as a base for disposing the single-wavelength light source 14, and a detector base 15a fixed to the base member 40a and serving as a base for disposing the scattered-light quantity detectors 15. Intensity of the light which has scattered from the sample to be analyzed is measured by at least two scattered-light detectors 15 arranged on a circumference with an optical axis of the single-wavelength light source 14 as the center. In the present embodiment, in addition to the scattered-light detectors 15 arranged on the optical axis, four more scattered-light detectors 15 are arranged on the circumference with the optical axis as the center. Only two of the four scattered-light detectors 15 are shown in FIG. 4. The four scattered-light detectors are arranged at the same tilt angle with respect to the optical axis. The tilt angle ranges from 0 to 30 degrees inclusive. The scattered-light detectors 15 and the light source 14 are arranged with the sample to be analyzed interposed. While a deterioration determining process described later herein uses the scattered-light detectors 15 arranged on the optical axis, the deterioration determining process does not necessarily use these detectors and may be executed using the scattered-light detectors 15 arranged on the circumference centering the optical axis. That is because the deterioration determining process can likewise be performed at tilt angles close to 0 degrees.

In the scattered-light quantity measuring unit 40, the incubator bath 3 is disposed between the single-wavelength light source 14 and the scattered-light quantity detectors 15 so as to extend in the circumferential direction of the reaction disk 1. An irradiation window 314 and a sensor window 315 are positioned on a line connecting the single-wavelength light source 14 and the scattered-light quantity detectors 15 inside the incubator bath 3. The irradiation window 314 transmits the single-wavelength light emitted from the single-wavelength light source 14 toward the reaction cuvette 2. The sensor window 315 allows the light to further pass through the reaction cuvette 2 and reach the scattered-light quantity detectors 15. The amount of transmitted light is detected whenever the reaction cuvette 2 driven in the circumferential direction of the reaction disk 1 inside the incubator bath 3 passes between the single-wavelength light source 14 and each scattered-light quantity detector 15. The amount of scattered light that the scattered-light quantity detector 15 has thus detected, that is, a detection result, is converted into a digital form by the A/D converter 16 and then sent to the computer 18 via the interface 19.

The reaction cuvette 2 containing the analyzed sample (the mixed reaction solution) is cleaned at a cleaning position by a cleaning mechanism 17.

The automatic analyzer further includes a keyboard 24 serving as an input device, a CRT display 25 as a display device, a printer 22 as a printout device, a recording media drive 23 as a device to record information on external output media such as FDs, and a memory 11 as a storage device (storage unit). These elements of the analyzer are connected to various functional sections including the computer 18 via the interface 19. The memory 11 is a storage device, such as a hard disk, for storing various information such as passwords set on an operator-by-operator basis, screen display levels, analytical parameters, analytical request item details, and calibration results in addition to analytical results. Past measurement results obtained at reference points in time, measurement results obtained during the execution of the deterioration determining process, and other results of the cell blank measurements to be described later herein are also stored in association with respective measuring dates/time and other information into the memory 11. Other such data as threshold data used during the deterioration determining process is stored in the memory 11 as well.

The computer 18 has a function of control means, which controls operation of the entire automatic analyzer. The computer 18 also has a measuring control unit 18a that controls the transmitted-light quantity detection process, the scattered-light quantity detection process, and measurement processes such as the cell blank measurements relating to the detection processes. In addition, the computer 18 has an arithmetic unit 18b that computes differences between the memory-stored measurement results of the past measurements at the reference points in time and the memory-stored measurement results obtained during the execution of the deterioration determining process. The computer 18 further has a determining unit 18c that performs the deterioration determining process to determine deterioration states of the single-wavelength light source 14, multi-wavelength light source 44, reaction cuvette 2, and the like in accordance with the result of cell blank measurement and arithmetic operation results by the arithmetic unit 18b.

In accordance with a command entered with the keyboard 24 or the like by an operator, the measuring control unit 18a performs the transmitted-light quantity detection process and the scattered-light quantity detection process upon the sample to be analyzed. Thus, qualitative/quantitative analysis of the sample is performed. In addition, the measuring control unit 18a conducts the cell blank measurements to be described later. The measuring control unit 18a further determines status of the automatic analyzer by executing a deterioration determining process based upon results of the cell blank measurements. The operator performs appropriate maintenance of the automatic analyzer according to particular results of the deterioration determining process, thereby suppressing decreases in analytical parameters and improving reliability of analytical results.

The transmitted-light quantity detection process, scattered-light quantity detection process, cell blank measurements, and deterioration determining process conducted by the measuring control unit in the automatic analyzer of the present embodiment will be described in further detail below. Maintenance support processes that support the maintenance based upon results of the deterioration determining process will also be described below.

(1) Transmitted-Light Quantity Detection Process

In the transmitted-light quantity detection process, at the moment a reaction cuvette 2 is passing through a measuring position on a line connecting the multi-wavelength light source 44 and the transmitted-light quantity detector 45, the transmitted-light quantity measuring unit 41 detects the amount of light transmitted through the multi-wavelength light source 44 first and then the reaction cuvette 2 to reach the transmitted-light quantity detector 45. The amount of transmitted light that the transmitted-light quantity detector 45 has thus detected, that is, a detection result, is converted into a digital form by the A/D converter 16, then sent to the computer 18 via the interface 19, and stored in association with a date/time of the measurement and other information into the memory (storage unit) 11.

When a reagent that specifically reacts with a desired biochemical component of a quantitative analyte in a sample stored in a sample container 2 is mixed into the sample, a reaction occurs that is commensurate with a quantity of the desired component of the analyte of interest in the mixed reaction solution. Irradiating this reaction solution with light of a specific wavelength(s), therefore, allows the quantity of transmitted light of a single wavelength or a plurality of wavelengths to be measured and then the quantity of the desired component in the analyte to be determined from that measured value in accordance with the Lambert-Beer law. In other words, the quantity of the desired biochemical component in the sample can be determined by utilizing the fact that when light is caused to pass through the mixed reaction solution, an amount of the light transmitted will attenuate more as the desired component of the analyte in the reaction solution has a higher concentration. To be more specific, if a numerical expression dictating a relation between the quantity of transmitted light and the concentration of the analyte of interest in the reaction solution is prepared beforehand, the quantity of the desired biochemical component in the sample can be determined by applying the measured quantity of transmitted light to that relational expression.

The reaction solution used for such determination differs according to a kind of the biochemical component whose quantity is to be determined.

If the component whose quantity is to be determined is a substrate contained in the sample, a color reaction is caused using a reagent that contains enzyme which specifically reacts with the substrate, and then a quantity of the substrate, the biochemical component of interest, is determined by utilizing the fact that the quantity of transmitted light decreases as a degree of the coloration increases in accordance with the quantity of that component.

If the component whose quantity is to be determined is an antigen contained in the sample, agglutination is caused using a reagent that contains an antibody which specifically reacts with the antigen, and then a quantity of the antigen, the biochemical component of interest, is determined by utilizing the fact that the quantity of transmitted light decreases as a degree of the agglutination increases in accordance with the quantity of that component. If the component whose quantity is to be determined is an antibody contained in the sample, a quantity of the antigen is determined by causing agglutination using a reagent that contains an antigen which specifically reacts with the antibody. For example, if the component of interest is an antigen, since using a reagent having an antibody sensitized (bound) to surfaces of latex particles will aggregate the latex according to a reaction between the antigen and the antibody, an aggregate larger than a clump of antigen and antibody particles only will arise, which will in turn amplify changes in the quantity of light transmitted and enable more accurate detection results to be obtained.

The measuring control unit 18a of the computer 18 uses the quantity of transmitted light, stored in the memory (storage unit) 11, to compute absorbance of the mixed reaction solution housed in the reaction cuvette 2, the computed absorbance being to be used to determine the quantity of the desired biochemical component. As described above, the transmitted-light quantity measuring unit 41 and measuring control unit 18a in the present embodiment work together to constitute a function of a transmission photometer (absorption photometer).

(2) Scattered-Light Quantity Detection Process

In the scattered-light quantity detection process, after the emission of light from the single-wavelength light source 14, at the moment a reaction cuvette 2 is passing through a measuring position on a line connecting the single-wavelength light source 14 and the scattered-light quantity detector 15, the scattered-light quantity measuring unit 40 detects the amount of light scattered from the reaction cuvette 2 and then reaching the scattered-light quantity detector 15. The amount of scattered light that the scattered-light quantity detector 15 has thus detected, that is, a detection result, is converted into a digital form by the A/D converter 16, then sent to the computer 18 via the interface 19, and stored in association with a date/time of the measurement and other information into the memory (storage unit) 11.

In the scattered-light quantity detection process, as in the transmitted-light quantity detection process, a reagent that specifically reacts with a desired biochemical component of a quantitative analyte in a sample stored in a sample container 2 is mixed into the sample. This causes a reaction between the sample and the reagent. A resulting aggregate in the reaction solution is irradiated with light, after which a quantity of the light scattered will be measured and then a quantity of the component of interest will be calculated from the measured quantity of scattered light.

The measuring control unit 18a of the computer 18 uses the quantity of scattered light, stored within the memory (storage unit) 11, to compute intensity of the light scattered by the mixed reaction solution stored in the reaction cuvette 2, and then use this computed intensity value to determine the quantity of the desired biochemical component. As described here, the scattered-light quantity measuring unit 40 and measuring control unit 18a in the present embodiment work together to constitute a function of a light-scattering photometer.

(3) Cell Blank Measurements

Cell blank measurements mean conducting the transmitted-light quantity detection process and the scattered-light quantity detection process upon a reaction cuvette 2 containing a predetermined reference solution (e.g., pure water or purified water). Result of cell blank measurement relating to the transmitted-light quantity detection process, that is, the quantity of transmitted light, and result of cell blank measurement relating to the scattered-light quantity detection process, that is, the quantity of scattered light, are sent to the computer 18 and then stored in association with respective measuring dates/time and other information into the memory (storage unit) 11. The cell blank measurements are conducted by use of the scattered-light detectors arranged on the optical axis of the single-wavelength light source.

(4) Deterioration Determining Process

Figure 5:
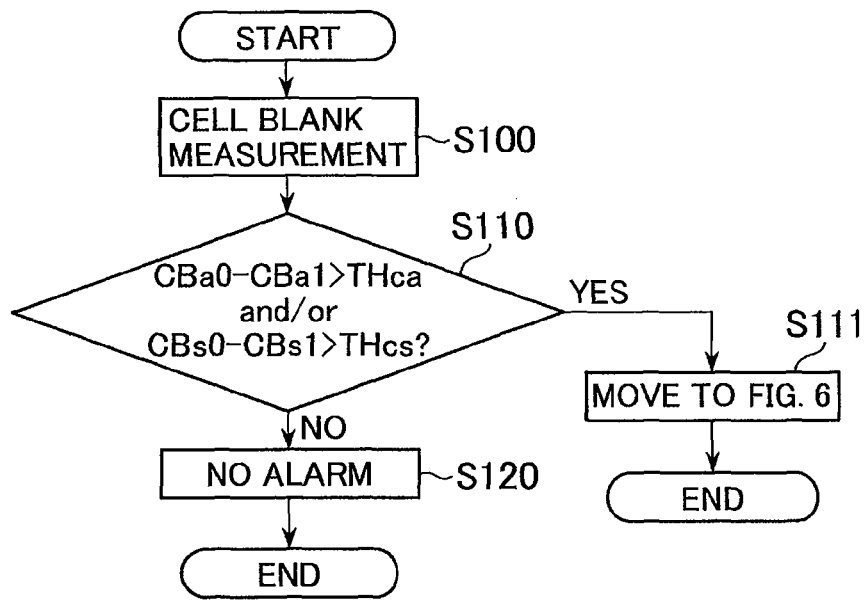
FIG. 5 is a flowchart of a deterioration determining process.

The deterioration determining process is to determine deterioration states of the single-wavelength light source 14, multi-wavelength light source 44, and reaction cuvette 2 in accordance with the result of cell blank measurement. The deterioration determining process will be described in detail below with reference to FIGS. 5 and 6. FIG. 5 is a flowchart showing the deterioration determining process in the present embodiment. FIG. 6 is a diagram showing an example of determination results on deterioration.

Probable causes of deterioration are listed below. Comparison with reference values in accordance with the flowchart of FIG. 5 allows identification of the assumed causes.

1. Dirt on irradiation windows (314, 344) or sensor windows (315, 345) of the scattered-light quantity measuring unit 41 and the transmitted-light quantity measuring unit 40, or dirt on irradiation window (314, 344) or sensor window (315, 345) of any measuring unit 2. Dirty reaction vessel 3. Dirty reaction cuvette 4. Malfunctioning of single-wavelength light source 14 and multi-wavelength light source 44, or malfunctioning of any light source Item 1 listed above may be conveniently expressed as dirty irradiation window(s) and dirty sensor window(s) hereinafter. This expression embraces a meaning of either the irradiation window or the sensor window being dirty, as well as a meaning of both the irradiation window and the sensor window being dirty.

Upon the operator entering a starting instruction for the deterioration determining process or upon a previously set starting time for the deterioration determining process, the measuring control unit 18a conducts the cell blank measurements (step S100). After this measurement, differences between result of cell blank measurement CBa1 corresponding to the transmitted-light quantity detection process and measurement results CBa0 corresponding to reference points in time are computed before it is determined whether computation results are greater than a predefined threshold value THca (step S110). Additionally, differences between result of cell blank measurement CBs1 corresponding to the scattered-light quantity detection process and measurement results CBs0 corresponding to reference points in time are computed before it is determined whether computation results are greater than a predefined threshold value THcs (step S110). If a result of the determination in step S110 is YES, then depending upon the deterioration determining results shown in FIG. 6, either a cell check alarm, a lamp check alarm, or an LED check alarm is issued (step S111) to complete the process. Conversely, if the result of the determination in step S110 is NO, no alarm is issued (step S120) to complete the process.

If either the irradiation window or sensor window of the transmitted-light quantity measuring unit is or both of these windows are dirty, this reduces the quantity of light transmitted and hence reduces CBa1. If either the reaction vessel or the reaction cuvette is dirty, or the multi-wavelength light source is malfunctioning, all of these states also lead to a decrease in CBa1. For these reasons, a condition of CBa0−CBa1>THca will be satisfied. Likewise, if either of or both of the irradiation window and sensor window of the scattered-light quantity measuring unit are dirty, this reduces the quantity of light scattered and hence reduces CBs1. If either the reaction vessel or the reaction cuvette is dirty, or the single-wavelength light source is malfunctioning, all of these states also lead to a decrease in CBs1. For these reasons, a condition of CBs0-CBs1>THcs will be satisfied. A cell check alarm is issued if the condition of CBa0-CBa1>THca and the condition of CBs0−CBs1>THcs are both satisfied.

The cell check alarm is an alarm in which it is suspected that there is dirt or deterioration relating primarily to the reaction cuvette (reaction cell) 2, and this alarm envisages the following cases:

1. Dirt on irradiation windows 314, 344 or sensor windows 315, 345 of the scattered-light quantity measuring unit 41 and the transmitted-light quantity measuring unit 40
2. Dirty incubator bath (reaction vessel) 3
3. Dirty reaction cuvette (reaction cell) 2
4. Malfunctioning of single-wavelength light source 14 and multi-wavelength light source 44

The quantity of light transmitted (or the absorbance) and the quantity of light scattered will decrease if either of or both of the irradiation windows 314, 344 and sensor windows 315, 345 of the scattered-light quantity measuring unit 41 and the transmitted-light quantity measuring unit 40 are dirty. A similar event will also arise if water in/from the reaction vessel is dirty. In addition, the quantity of light transmitted (or the absorbance) and light scattered will decrease if the single-wavelength light source 14 and the multi-wavelength light source 44 both deteriorate and the amount of light decreases. If an LED is used as the single-wavelength light source 14, however, since the LED is at least ten times as long in life as in a case that a halogen light source is used as the multi-wavelength light source 44, it is considered to be less likely for the single-wavelength light source 14 and the multi-wavelength light source 44 deteriorate at the same time. Accordingly, if the alarm is not caused by dirt on the irradiation windows 314, 344 and/or sensor windows 315, 345 of the scattered-light quantity measuring unit 41 and the transmitted-light quantity measuring unit 40 or by fouling of the reaction vessel water, then in consideration of the fact that the LED is much longer-lived as the single-wavelength light source 14, dirt on the reaction cuvette 2 is more likely to be causing the cell check alarm.

A lamp check alarm is issued if the conditions of CBa0−CBa1>THca and CBs0−CBs1≤=THcs are both satisfied. In this case, the dirt on the characteristic irradiation window and sensor window of the scattered-light quantity measuring unit 40 that relate to the measurement of the quantity of light scattered, and the malfunction in the single-wavelength light source are first excluded from consideration as probable/assumed causes of the alarm. The dirt on the reaction vessel and the reaction cuvette, both of which are common to the measurement of the quantity of light transmitted, are next excluded from consideration as probable/assumed causes of the alarm.

The lamp check alarm is an alarm in which it is suspected that there is dirt or malfunction relating to the transmitted-light quantity measuring unit 41, and this alarm envisages the following cases:

1. Dirt on irradiation window 344 and sensor window 345 of the transmitted-light quantity measuring unit 41
2. Malfunctioning of multi-wavelength light source 44

An LED check alarm is issued if the conditions of CBa0−CBa1≤=THca and CBs0−CBs1>THcs are both satisfied. In this case, as described in the above case, the above events specific to the measurement of the quantity of light transmitted, and the above events common to the measurement of the quantity of light scattered are excluded from consideration as probable/assumed causes of the alarm.

The LED check alarm is an alarm in which it is suspected that there is dirt or malfunction relating to the scattered-light quantity measuring unit 40, and this alarm envisages the following cases:

1. Dirt on irradiation window 314 and sensor window 315 of the scattered-light quantity measuring unit 40
2. Malfunctioning of single-wavelength light source 14

(5) Maintenance Support Processes

Process steps that will be executed if any one of the three kinds of check alarms is issued during the deterioration determining process will be described below with reference to FIGS. 7 to 13.

(5-1) Maintenance Support Process Corresponding to the Cell Check Alarm

Figure 7:
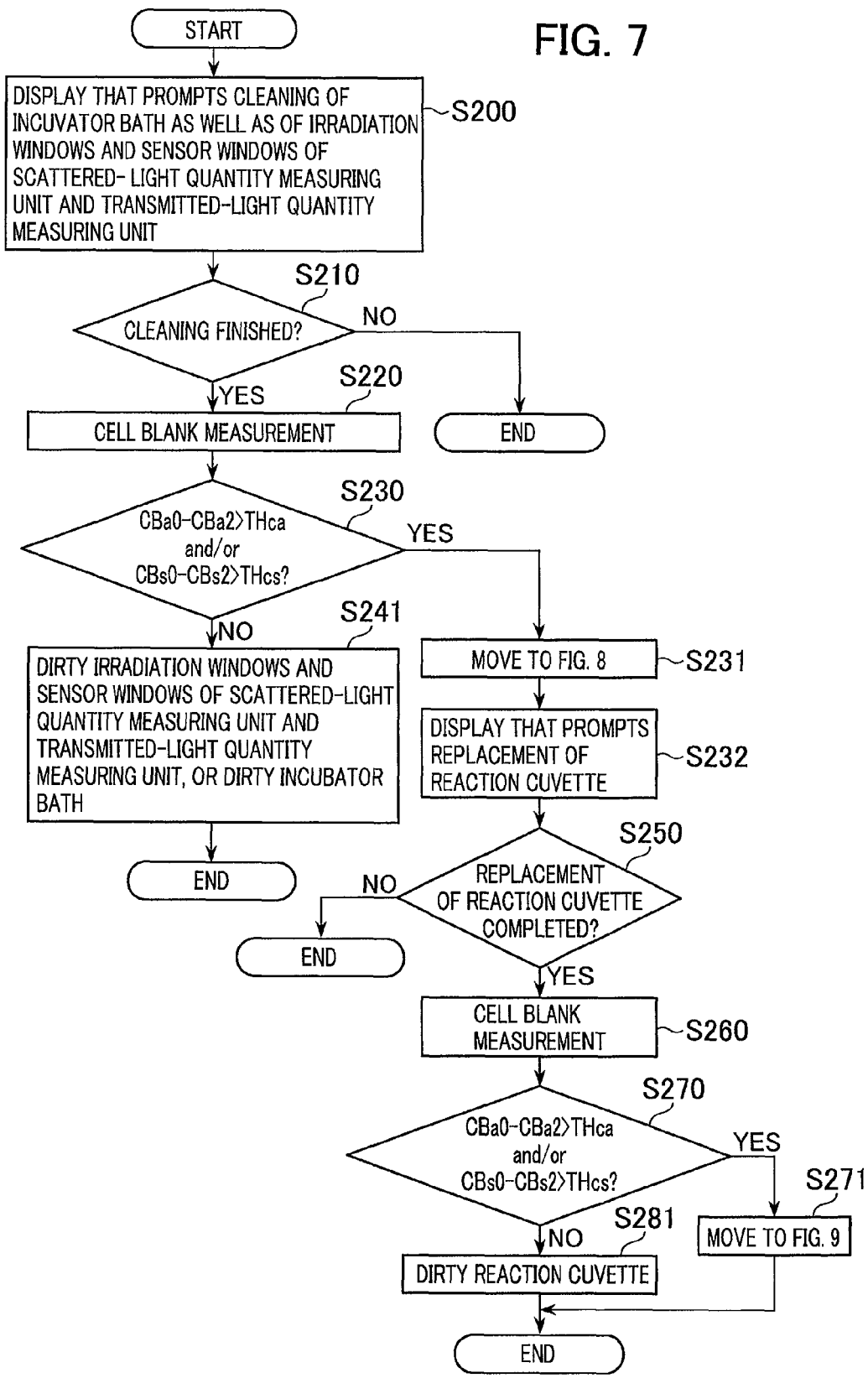
FIG. 7 is a flowchart of a maintenance support process relating to a cell check alarm.

FIG. 7 is a flowchart of the maintenance support process corresponding to the cell check alarm. FIG. 8 is a diagram showing another example of determination results on deterioration.

Upon the cell check alarm being issued, the measuring control unit 18a makes a display on the CRT display (display device) 25, prompting the operator to clean the incubator bath (reaction vessel) 3 as well as to clean the irradiation windows 314, 344 and sensor windows 315, 345 of the scattered-light quantity measuring unit 40 and the transmitted-light quantity measuring unit 41 (step S200). After this display, the measuring control unit 18a prompts the operator to confirm whether the cleaning has been completed (step S210). The maintenance support process terminates if a result of the confirmation is NO, that is, if the operator skips the cleaning and enters corresponding information with the keyboard 24 or the like.

If the result of the confirmation in step S210 is YES, that is, if the operator does the cleaning and enters corresponding information with the keyboard 24 or the like, then cell blank measurements are conducted (step S220). Subsequently, differences between result of cell blank measurement CBa2 corresponding to the transmitted-light quantity detection process and measurement results CBa0 corresponding to reference points in time are computed before it is determined whether computation results are greater than the predefined threshold value THca (step S230). Additionally, differences between result of cell blank measurement CBs2 corresponding to the transmitted-light quantity detection process, and measurement results CBs0 corresponding to reference points in time, are computed before it is determined whether computation results are greater than the predefined threshold value THcs (step S230). If a result of the determination in step S230 is NO, information indicating that either dirt on irradiation windows 314, 344 and sensor windows 315, 345 of the scattered-light quantity measuring unit 40 and the transmitted-light quantity measuring unit 41 or dirt in incubator bath (reaction vessel) 3 has caused the cell check alarm is displayed on the CRT display (display device) 25, in step S241. The maintenance support process is then terminated.

If the determination result in step S230 is YES, then in accordance with deterioration determining results shown in FIG. 8, assignable causes of the deterioration are identified (step S231) and these deterioration causes are displayed on the CRT display (display device) 25 to terminate the maintenance support process.

In the above case, the cleaning of the reaction vessel and that of the irradiation windows and sensor windows of the scattered-light quantity measuring unit and the transmitted-light quantity measuring unit have already been completed. In addition, in FIG. 8 the dirt relating to these sections of the automatic analyzer has been excluded as part of the probable/assumed causes. At least one of the deterioration causes in FIG. 8 can therefore be identified.

Furthermore, if the conditions of CBa0–CBa2>THca and CBs0–CBs2>THcs are both satisfied, since probable/assumed causes are that the reaction cuvette is dirty and that the single-wavelength light source and the multi-wavelength light source are malfunctioning, it cannot be determined which of the two events is more likely to have caused the alarm. Given that the two conditions are both satisfied, therefore, which of the two probable/assumed causes is really a cause can be determined by making a display that prompts replacement of the reaction cuvette, making the operator replace the reaction cuvette and conducting further cell blank measurements.

Given that the conditions of CBa0–CBa2>THca and CBs0–CBs2>THcs are both satisfied, the display prompting the replacement of the reaction cuvette 2 appears on the CRT display (display device) 25 in step S232. After this display, the measuring control unit 18a prompts the operator to confirm whether the replacement of the reaction cuvette 2 has been completed (step S250). The maintenance support process terminates if a result of the confirmation is NO, that is, if the operator skips the replacement of the reaction cuvette and enters corresponding information with the keyboard 24 or the like.

If the result of the confirmation in step S250 is YES, that is, if the operator replaces the reaction cuvette and enters corresponding information with the keyboard 24 or the like, then cell blank measurements are conducted (step S260). Subsequently, differences between result of cell blank measurement CBa3 corresponding to the transmitted-light quantity detection process and measurement results CBa0 corresponding to reference points in time are computed before it is determined whether computation results are greater than the predefined threshold value THca. Additionally, differences between result of cell blank measurement CBs3 corresponding to the transmitted-light quantity detection process and measurement results CBs0 corresponding to reference points in time are computed before it is determined whether computation results are greater than the predefined threshold value THcs (step S270).

If a result of the determination in step S270 is NO, information indicating that dirty reaction cuvette 2 has caused the cell check alarm is displayed on the CRT display (display device) 25 in step S281. The maintenance support process is then terminated.

If the determination result in step S270 is YES, then in accordance with deterioration determining results shown in FIG. 9, assignable causes of the deterioration are identified (step S271) and these deterioration causes are displayed on the CRT display (display device) 25 to terminate the maintenance support process. Which of the multi-wavelength light source and the single-wavelength light source is malfunctioning, however, was determined in FIG. 8, such that both of the multi-wavelength light source and the single-wavelength light source are most likely to be malfunctioning. In step S270, therefore, if either the cell blank measurements associated with the transmitted-light quantity detection process or the cell blank measurements associated with the scattered-light quantity detection process are executed, it can be determined whether the reaction cuvette 2 is dirty or the malfunction relating to the light sources is occurring. For this reason, execution of one of the two kinds of cell blank measurements may replace the execution of both kinds of cell blank measurements.

(5-2) Maintenance Support Process Corresponding to the Lamp Check Alarm

FIG. 10 is a flowchart of the maintenance support process corresponding to the lamp check alarm. FIG. 11 is a diagram showing a further example of determination results on deterioration.

Upon the lamp check alarm being issued, the measuring control unit 18a makes a display on the CRT display (display device) 25, prompting the operator to clean the irradiation window 344 and sensor window 345 of the transmitted-light quantity measuring unit 41 (step S300). After this display, the measuring control unit 18a confirms with the operator whether cleaning has been completed (step S310). The maintenance support process terminates if a result of the confirmation is NO, that is, if the operator skips cleaning and enters corresponding information with the keyboard 24 or the like.

If the result of the confirmation in step S310 is YES, that is, if the operator executes cleaning and enters corresponding information with the keyboard 24 or the like, then cell blank measurements are conducted (step S320). Subsequently, differences between result of cell blank measurement CBa4 corresponding to the transmitted-light quantity detection process and measurement results CBa0 corresponding to reference points in time are computed before it is determined whether computation results are greater than the predefined threshold value THca (step S330). If a result of the determination in step S330 is NO, information indicating that dirty irradiation window 344 and sensor window 345 of the transmitted-light quantity measuring unit 41 has caused the lamp check alarm is displayed on the CRT display (display device) 25 in step S332. The maintenance support process is then terminated.

If the result of the determination in step S330 is YES, it is determined that malfunctioning of multi-wavelength light source 44 is most likely to have caused the lamp check alarm. This is therefore displayed on the CRT display (display device) 25 in step S331 to complete the maintenance support process.

(5-3) Maintenance Support Process Corresponding to the LED Check Alarm

FIG. 12 is a flowchart of the maintenance support process corresponding to the LED check alarm. FIG. 13 is a diagram showing a further example of determination results on deterioration.

Upon the LED check alarm being issued, the measuring control unit 18a makes a display on the CRT display (display device) 25, prompting the operator to clean the irradiation window 314 and sensor window 315 of the scattered-light quantity measuring unit 40 (step S400). After this display, the measuring control unit 18a confirms with the operator whether cleaning has been completed (step S410). The maintenance support process terminates if a result of the confirmation is NO, that is, if the operator skips cleaning and enters corresponding information with the keyboard 24 or the like.

If the result of the confirmation in step S410 is YES, that is, if the operator executes cleaning and enters corresponding information with the keyboard 24 or the like, then cell blank measurements are conducted (step S420). Subsequently, differences between result of cell blank measurement CBs5 corresponding to the scattered-light quantity detection process and measurement results CBs0 corresponding to reference points in time are computed before it is determined whether computation results are greater than the predefined threshold value THcs (step S430). If a result of the determination in step S430 is NO, information indicating that dirty irradiation window 314 and sensor window 315 of the scattered-light quantity measuring unit 40 has caused the LED check alarm is displayed on the CRT display (display device) 25 in step S432. This terminates the maintenance support process.

If the result of the determination in step S430 is YES, it is determined that Malfunctioning of single-wavelength light source 14 is most likely to have caused the LED check alarm. This is therefore displayed on the CRT display (display device) 25 in step S431 to complete the maintenance support process.

Advantageous effects of the present embodiment having the above configuration will be described below.

Automatic analyzers use various ways to have qualitative/quantitative analysis of such biological samples as of blood and urine. An example of its method is known to conduct the qualitative/quantitative analysis of samples by measuring the amount of light transmitted through a mixed reaction solution of the sample and a reagent or by measuring the amount of light scattered by the reaction solution. In these automatic analyzers employing conventional techniques, a reaction cuvette blank value that rises up with increasing changes in absorbance of a light beam passed through the reaction cuvette is compared with a plurality of determination criteria including a predefined different blank reference value for each of analytical items. After that, it is determined whether a reaction cuvette for causing a reaction between a sample and a reagent and analyzing the sample can be actually used for measurement. That is to say, the determination of the reaction cuvette for usability is based primarily upon comparison results obtained from those comparisons. However, in addition to a state of the reaction cuvette, a variety of other factors are involved with analytical accuracy of the automatic analyzer used for the qualitative/quantitative analysis of the sample. This has made it difficult to maintain high analytical accuracy by merely determining the reaction cuvette for usability, as in the above conventional techniques.

In contrast to this, the automatic analyzer of the present embodiment is configured so that the deterioration states of the single-wavelength light source 14, multi-wavelength light source 44, and reaction cuvette 2 are determined on the basis of the result of cell blank measurement obtained in the transmitted-light quantity measuring unit 41 and the scattered-light quantity measuring unit 40. With this configuration, in addition to a state of the reaction cuvette a variety of other factors can be estimated and hence a decrease in analytical accuracy can be suppressed.

REFERENCE NUMERALS

1 Reaction disk
2 Reaction cuvette (Reaction cell)
3 Incubator bath (Reaction vessel)
5 Samples disk
7 Sampling mechanism
9A, 9B Reagent disk
10A, 10B Reagent bottles
11 Memory
12A, 12B Reagent dispensing mechanisms
13A First reagent disk
13B Second reagent disk
14 Single-wavelength light source
14a Light source base
15 Scattered-light quantity detector
15a Detector base
16 A/D converter
18 Computer
18a Measuring control unit
18b Arithmetic unit
18c Determining unit
19 Interface
20 Sampling control unit
21 Reagent dispensing control unit
22 Printer
23 Recording medium drive
24 Keyboard
25 CRT display
33A, 33B Stirring mechanisms
34A, 34B Readers
40 Scattered-light quantity measuring unit
41 Transmitted-light quantity measuring unit
41a Base member
44 Multi-wavelength light source
44a Light source base
45 Transmitted-light quantity detector
45a Detector base
314, 315 Irradiation window
344, 345 Sensor window

The invention claimed is:

1. An automatic analyzer comprising:
a multi-wavelength light source that irradiates with multi-wavelength light a reaction cuvette containing a liquid mixture of a sample to be analyzed and a reagent;
transmitted-light quantity detection means that detects an amount of light transmitted through the reaction cuvette and internal contents of the reaction cuvette;
a single-wavelength light source that irradiates the reaction cuvette with single-wavelength light;
scattered-light quantity detection means that detects an amount of single-wavelength light scattered from the reaction cuvette and the internal contents of the reaction cuvette;
a storage unit that stores a result of the transmitted-light quantity detection with the transmitted-light quantity detection means and a result of the scattered-light quantity detection with the scattered-light quantity detection means; and
a determining unit that performs a deterioration determining process to determine deterioration states of the single-wavelength light source, multi-wavelength light source, and reaction cuvette in accordance with measurement results of cell blank measurements conducted on the reaction cuvette where a predetermined reference solution is stored to detect an amount of light transmitted through and an amount of light scattered from.

2. The automatic analyzer according to claim 1, further comprising:
an arithmetic unit that computes differences between a first measurement result and a second measurement result of cell blank measurements,
wherein the first measurement result is from a cell blank measurement conducted at predefined reference points in time that are earlier than when cell blank measurements intended for the deterioration determining process are conducted, the first measurement result being stored in the storage unit,
wherein the second measurement result is from a cell blank measurement intended for the deterioration determining process, and
wherein the determining unit performs the deterioration determining process on a basis of a computation result by the arithmetic unit.

3. The automatic analyzer according to claim 2,
wherein if deterioration of the reaction cuvette is determined to have begun during the deterioration determining process, the determining unit issues a cell check alarm signal to inform an operator that an error relating to the reaction cuvette has occurred.

4. The automatic analyzer according to claim 2,
wherein if deterioration of the single-wavelength light source is determined to have begun during the deterioration determining process, the determining unit issues a single-wavelength light source check alarm signal to inform the operator that an error relating to the single-wavelength light source has occurred.

5. The automatic analyzer according to claim 2,
wherein if deterioration of the multi-wavelength light source is determined to have begun during the deterioration determining process, the determining unit issues a multi-wavelength light source check alarm signal to inform the operator that an error relating to the multi-wavelength light source has occurred.

* * * * *